United States Patent [19]
Buxton

[11] Patent Number: 6,098,446
[45] Date of Patent: Aug. 8, 2000

[54] ON HEAD VALVE SPRING TESTER

[76] Inventor: Bradley S. Buxton, 1322 Old Rockport Rd., Boonville, Ind. 47601

[21] Appl. No.: 08/968,257

[22] Filed: Nov. 12, 1997

Related U.S. Application Data

[60] Provisional application No. 60/030,471, Nov. 13, 1996.
[51] Int. Cl.[7] ................................................. G01L 27/00
[52] U.S. Cl. ............................ 73/1.72; 73/161; 73/118.1; 73/865.9
[58] Field of Search ..................... 73/1.72, 161, 118.1, 73/865.9

[56] References Cited

U.S. PATENT DOCUMENTS

| | | | |
|---|---|---|---|
| 3,640,129 | 2/1972 | Bandimere | 73/161 |
| 4,641,521 | 2/1987 | Lawrence | 73/161 |

OTHER PUBLICATIONS

Catalog entitled Race Proven Moroso Performance Products—20th Anniversary, 1988, Moroso Performance Products, Inc., Guilford, CT, p. 64.

*Primary Examiner*—Hezron Williams
*Assistant Examiner*—Thuy Vinh Tran
*Attorney, Agent, or Firm*—Baker & Daniels

[57] ABSTRACT

An apparatus for on head testing of a valve spring that biases a rocker arm assembly. The testing apparatus includes a trunnion body portion that is pivotally connected to a main body portion. A biasing member is movably mounted to the main body portion and abuts a first rocker arm of the rocker arm assembly during use. A latch member engageable with a second rocker arm of the rocker arm assembly is adjustably mounted to the trunnion body portion to permit different spacings with the biasing member to be furnished to accommodate different sized rocker arms. When a tester handle is used to drive the biasing member toward the first rocker arm during valve spring testing, the force applied by the biasing member to compress the valve spring is measured by the sensing of the movement of the biasing member relative to the main body portion, and is displayed on a gauge mounted on the main body portion.

12 Claims, 10 Drawing Sheets

ON HEAD VALVE SPRING TESTER

CROSS-REFERENCE TO RELATED APPLICATION

This application claims the benefit under 35 U.S.C. § 119(e) of United States Provisional Application No. 60/030,471, filed Nov. 13, 1996.

BACKGROUND OF THE INVENTION

The present invention pertains to spring testing devices, and, in particular, to an apparatus for testing valve springs installed in vehicle engines.

In a variety of engines, for example race car engines, springs are used to bias valves within the engine block which are actuated by rocker arms and push rods. Over time, these valve springs can fatigue or otherwise deteriorate. As a result, the valves will not be biased with the optimal force, and consequently the operation of the vehicle engine may be compromised.

Prior art devices developed to test the strength of the valve springs without removing or otherwise disassembling the springs from the engine suffer from shortcomings which limit their utility. For example, one known type of valve seat pressure tester comprises a gripper body from which separately extend a rigid needle member and a flexible bar. Attached to the flexible bar are a hand grip and a scale. When the gripper body is arranged for use on a rocker arm assembly and as a user applies force on the hand grip until the rocker arm biasing valve spring is caused to compress, the bar flexes and the scale moves relative to the needle member. The needle member points to indicia on the scale, and the user can then read the scale to assess the spring force of the valve spring. Because the gripper body is intended to be a universal fit and is not adjustable to properly adapt for different sized rocker arms, the spring force measurements resulting from this type of device may be less accurate than desired.

Thus, it would be desirable to provide an apparatus that allows for the testing of a valve spring in a convenient and accurate fashion without requiring removal of the valve spring from the engine.

SUMMARY OF THE INVENTION

The present invention provides an apparatus adapted to fit over and engage a valve spring biased rocker arm assembly in order to test the associated valve spring. The invention is adjustable to fit properly over a range of different sized rocker arms, and the force sensing mechanism that it employs allows the strength of that valve spring to be accurately determined empirically.

In one form thereof, the present invention provides an apparatus for on head testing of a valve spring that biases a rocker arm assembly, including a body, a biasing member connected to the body and engageable with a first rocker arm of the rocker arm assembly, a latch member connected to the body and engageable with a second rocker arm of the rocker arm assembly, wherein at least one of the latch member and the biasing member is structured and arranged to be movable relative to the body to alter a spacing between the latch member and the biasing member for accommodating different length rocker arms, a handle connected to either the latch member or the body for driving the biasing member toward the first rocker arm during valve spring testing, and an indicator for measuring and displaying a force applied on the rocker arm assembly to compress the valve spring during valve spring testing.

In another form thereof, the present invention provides an on head valve spring tester including a body, a biasing member movably mounted to the body and adapted for abutting engagement with a first rocker arm of the rocker arm assembly with which the tester is utilized, a latch member extending from the body for engagement with a second rocker arm, and a handle connected to either the latch member or the body for driving the biasing member in a first direction toward the first rocker arm during valve spring testing. The biasing member is movable relative to the body in a direction generally opposite to the first direction from a first position toward a second position during biasing engagement with the first rocker arm during valve spring testing. The tester also includes an indicator adapted to detect movement of the biasing member from the first position toward the second position and provide a display indicative of a force required to so move the biasing member.

In still another form thereof, the present invention provides an on head valve spring tester including a handle, means for attaching to a first rocker arm, means, operable by the handle, for biasing a second rocker arm fixedly connected with the first rocker arm, and means for displaying a force applied by the biasing means on the second rocker arm.

One advantage of the valve spring tester of the present invention is that it may be easily used without requiring disassembly of the valve spring from the remainder of the engine.

Another advantage of the valve spring tester of the present invention is that it permits accurate measurements of the spring force of a valve spring.

Still another advantage of the valve spring tester of the present invention is that it is adjustable to be operatively fitted on different sized rocker arms.

BRIEF DESCRIPTION OF THE DRAWINGS

The above-mentioned and other advantages and objects of this invention, and the manner of attaining them, will become apparent and the invention itself will be better understood with reference to the following description of embodiments of the invention taken in conjunction with the accompanying drawings, wherein.

Corresponding reference characters indicate corresponding parts throughout the several views. Although the drawings represent embodiments of the present invention, the drawings are not necessarily to scale and certain features may be exaggerated or omitted in some of the drawings in order to better illustrate and explain the present invention.

DESCRIPTION OF THE PREFERRED EMBODIMENTS

Referring now to FIGS. 1–6, there are shown various views of a first embodiment of an on head valve spring tester, generally designated 20, according to the present invention. Tester 20 includes an inclined handle arm 22 to which a perpendicularly oriented handle grip 24 is fixedly attached with screw 26. Handle arm 22 is pivotally mounted on a steel pivot shaft 28 transversely extending through a bore provided in the base of handle arm 22. Handle arm 22 and handle grip 24, as well as other structural portions of the tester such as the trunnion body and main body, are made of machined, anodized aluminum, but other sufficiently strong and preferably lightweight materials may be employed within the scope of the invention. Flanking both sides of handle arm 22, screws 30 downwardly extend through the exposed ends of steel pivot shaft 28 and through spacers 32 into tapped bores provided in the top surface of trunnion body 34. A first end of aluminum calibration link 40 is pivotally secured to pivot mount 36 with friction fit pivot pin 42. Pivot mount 36 fits into recess 38 in handle arm 22. For purposes described below, pivot mount 36 is adjustably secured along the height of handle arm 22 by way of screw 44 that fits within handle recess 46 and which extends into a tapped bore formed in the rear portion of pivot mount 36.

Rocker latch member 48 extends downwardly below trunnion body 34. Lip 50 of latch member 48 is designed to engage the underside of a valve actuating rocker arm as described further below. Four steel guide pins 52 secured to rocker latch member 48 are arranged in a square pattern and project into smooth guide bores provided in the rear end of trunnion body 34.

Adjustment screw 54 extends through latch member 48 and inserts into a tapped bore provided in the rear end of trunnion body 34. Rotation of adjustment screw 54 in either direction causes latch member 48 to be selectively moved either to the left or right (from the perspective of a FIG. 1 viewer) to adjust the position or spacing of latch member 48 relative to trunnion body 34. This adjustability, which covers a range of preferably at least one-half inch, allows tester 20 to accommodate different sized rocker arms. In an alternate embodiment (see FIG. 10), the adjustment screw may be equipped with a rearwardly projecting knob, grippable between the thumb and forefinger of a user, to facilitate its adjustment.

Figure 9:
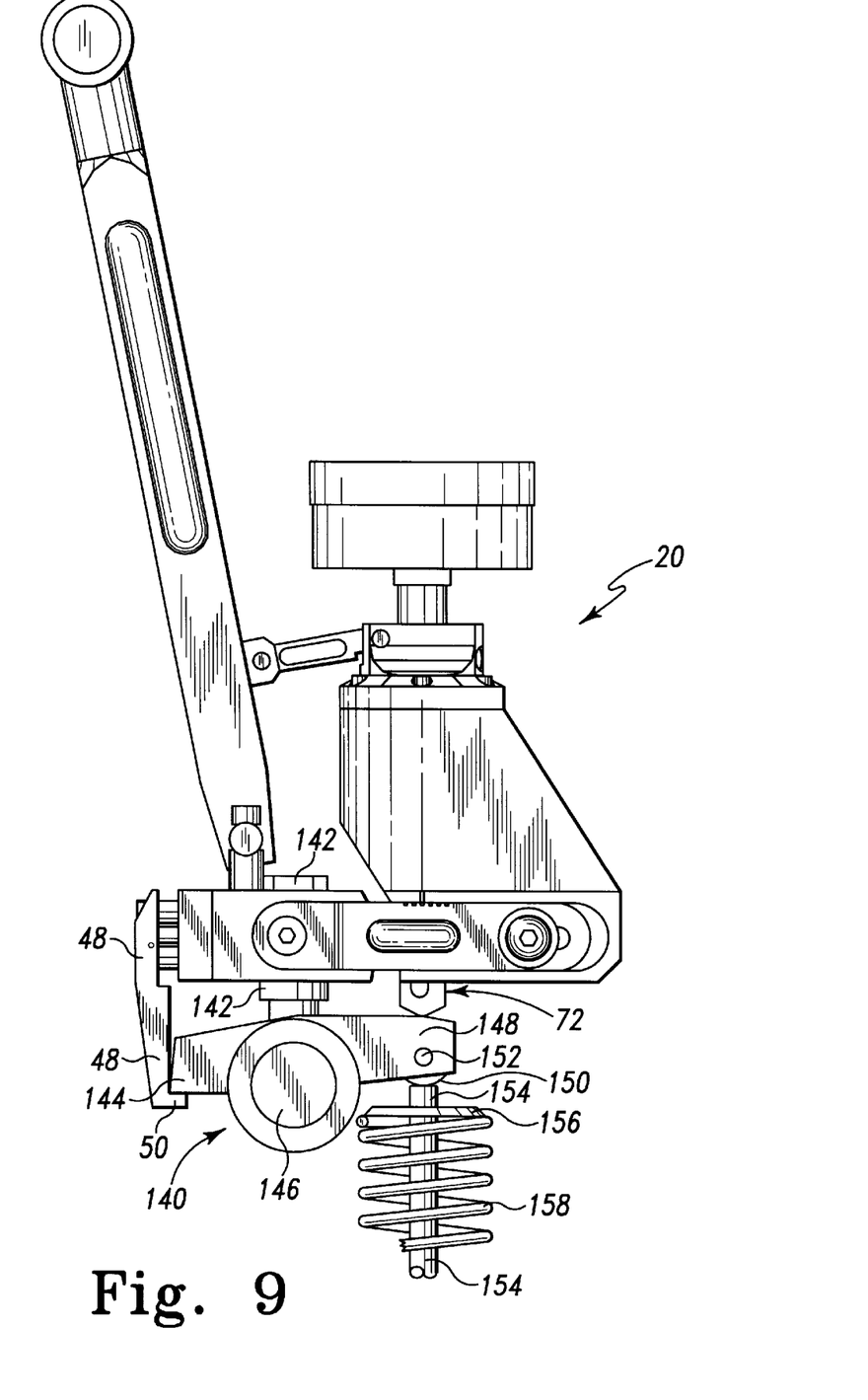
FIG. 9 is a side view of the valve spring tester of FIG. 1 operationally mounted on a valve shifting rocker arm assembly biased by a valve spring to be tested.

Trunnion body 34 includes a vertically oriented, central opening 56 extending entirely through the body height. Opening 56 is adapted to insertably receive a rocker arm stud secured to the cylinder head as described further below. In situations where projecting rocker arm studs are shorter than as shown in FIG. 9 or entirely absent, opening 56 may be replaced with a recess in the trunnion body underside or eliminated entirely while still allowing tester 20 to be operated in a proper fashion. On either of its sides, trunnion body 34 is provided with tapped bores which threadedly receive stripper bolts 60 used to secure flanking connecting arms 62. Stripper bolts 60 allow connecting arms 62 to pivot relative to trunnion body 34. In an alternate embodiment, these tapped bores may be replaced with smooth bores into which friction fit the inward ends of a pair of pins. To permit pivoting of the body portions, the outward pin ends of this alternate embodiment freely rotate within bushings press fit into bores provided in the connecting arms 62.

Figure 6:
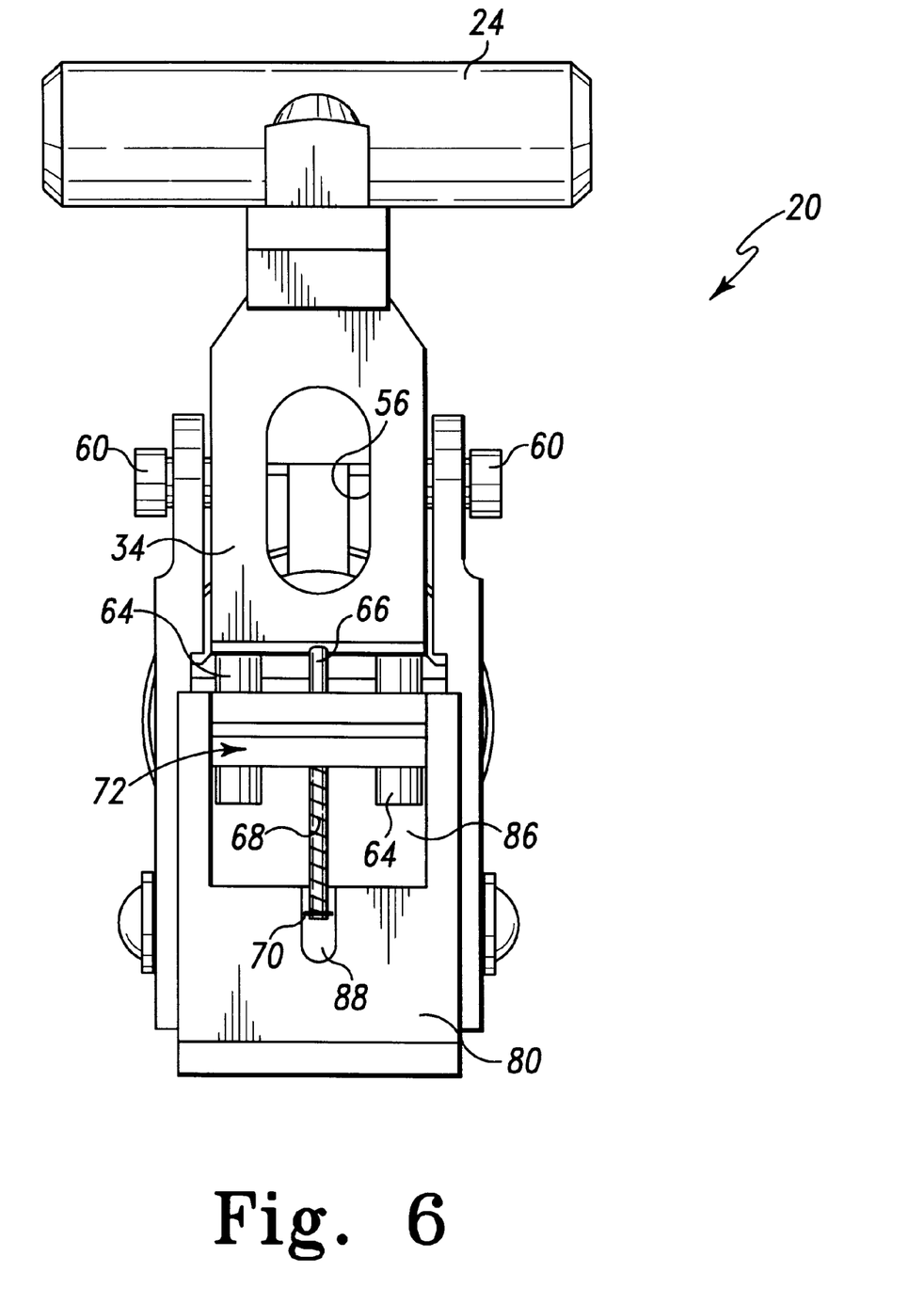
FIG. 6 is a bottom view of the valve spring tester of FIG. 1.

As further shown in FIG. 6, a pair of cylindrical, steel guide pins 64 project from the forward surface of trunnion body 34. Between guide pins 64, steel rod 66 similarly projects from trunnion body 34. Rod 66 includes a retainer ring 70 fixedly secured to the rod distal end. Rod 66 extends through compression spring 68, which abuts retaining ring 70 and the face of a rocker block assembly, which is generally designated 72 and described more fully below. Guide pins 64 and rod 66 are secured to trunnion body 34 via a friction fit or with not shown set screws.

Figure 10:
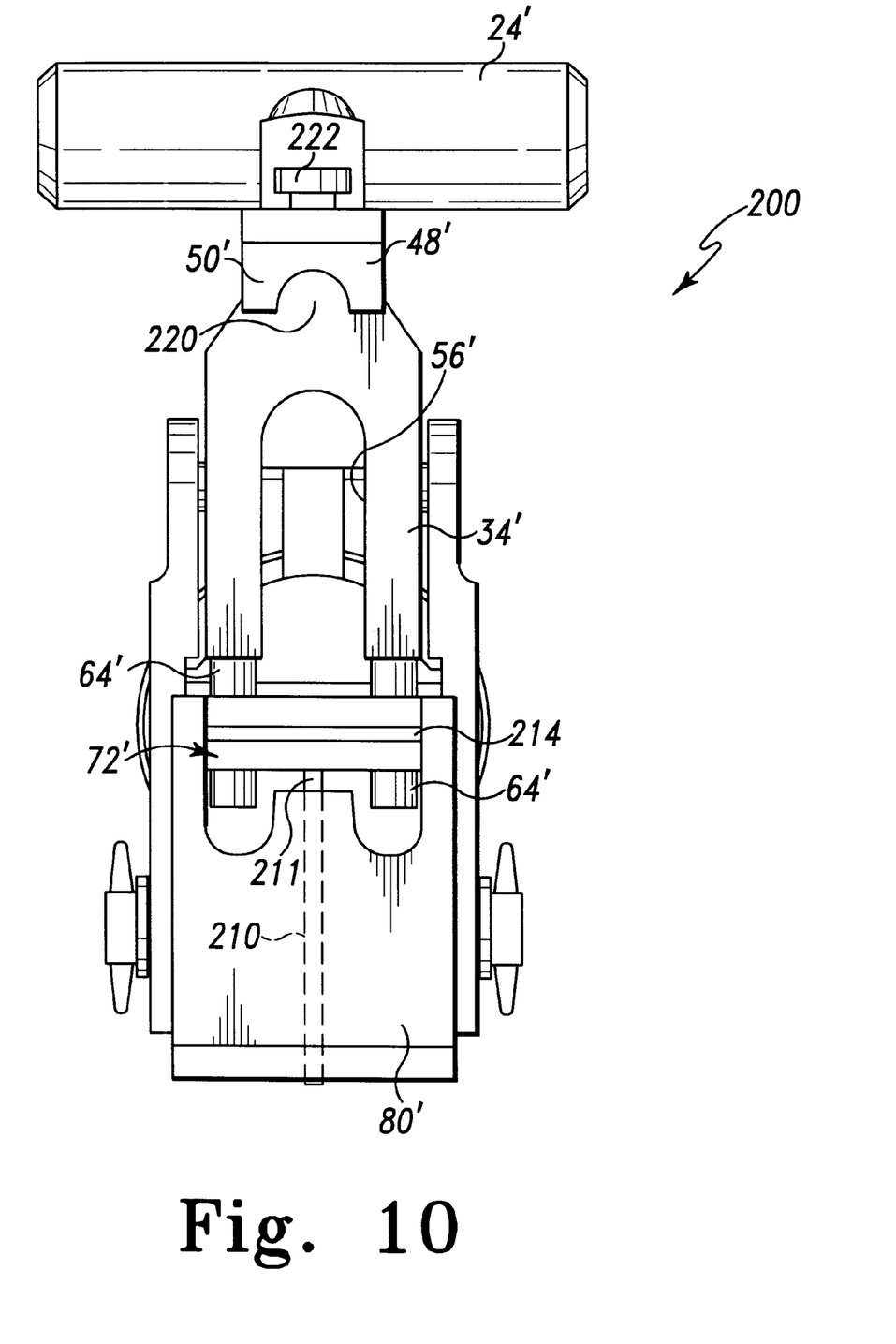
FIG. 10 is a bottom view of an alternate embodiment of a valve spring tester of the present invention.

Each aluminum connecting arm 62 includes a horizontal adjustment slot 74 through which button head cap screws 76 with washers extend. Cap screws 76 may be replaced with winged thumb screws in alternate embodiments as shown in FIG. 10. The threaded shafts of cap screws 76 threadedly engage tapped bores provided in the sides of tester main body 80. When both button head cap screws 76 are loosened, screws 76 may be moved along slots 74 such that main body 80 may be shifted to the right or left (from the perspective of a FIG. 1 viewer) relative to trunnion body 34. Each connecting arm 62 fits within a recess 82 provided in the sides of main body 80. On each side of main body 80, a groove 84 is formed along the body shoulder which defines recess 82. Grooves 84 are adjacent to a series of grooves or notches 78 provided along the upper edge of each connecting arm 62. Grooves 78, 84, for which different types of indicia included printed markings could be substituted, provide a visual indication to a user of the distances between trunnion body 34 and main body 80, and more particularly the distance between bolts 60 and rocker contacting face 97.

Figure 7:
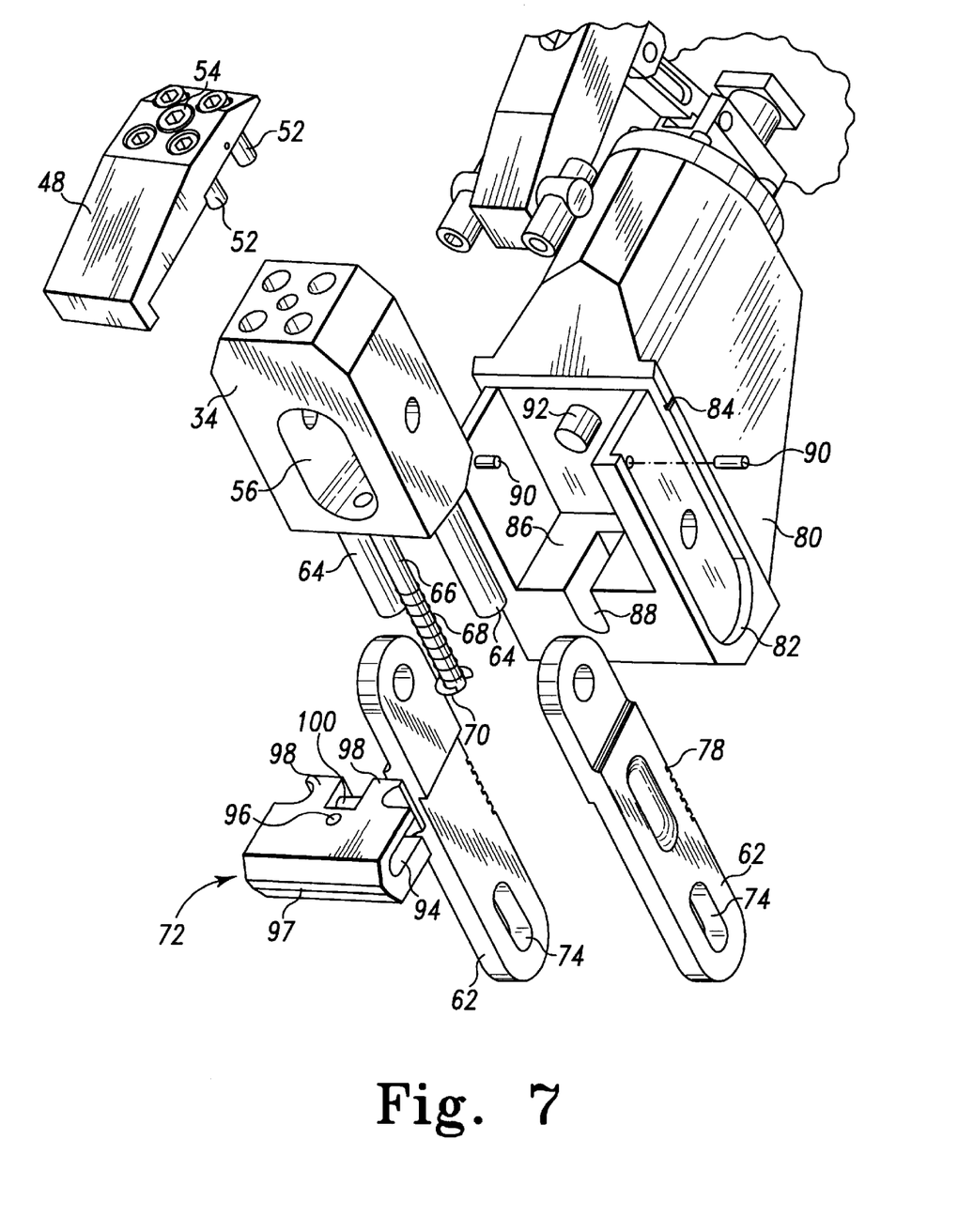
FIG. 7 is an exploded perspective view of portions of the valve spring tester of FIG. 1.

As best shown in FIG. 6 and the partial exploded view of FIG. 7, the underside of main body 80 is provided with a cavity 86 into which clearance space 88 for rod 66 opens. Alignment pins 90 project into cavity 86 and are secured to main body 80 via an interference fit. The distal end of piston shaft 92 projects from above into cavity 86. Rocker block assembly 72 is made of aluminum and includes slots 94 on both of its sides into which alignment pins 90 extend when assembled. Pins 90 cooperate with slots 94 to ensure rocker block assembly 72 remains below piston shaft 92 during movement of main body 80 relative to trunnion body 34. Bore 96 is sized to slidably receive rod 66 therethrough, but is small enough to prevent the insertion of rod-mounted spring 68. Rocker block assembly 72 includes a flat, rocker contacting face 97 and ears 98 having arcuate outer sides adapted to slide over guide pins 64. A needle bearing 100 spans ears 98 and is directly engaged by piston shaft 92 when tester 20 is fully assembled.

Figure 8:
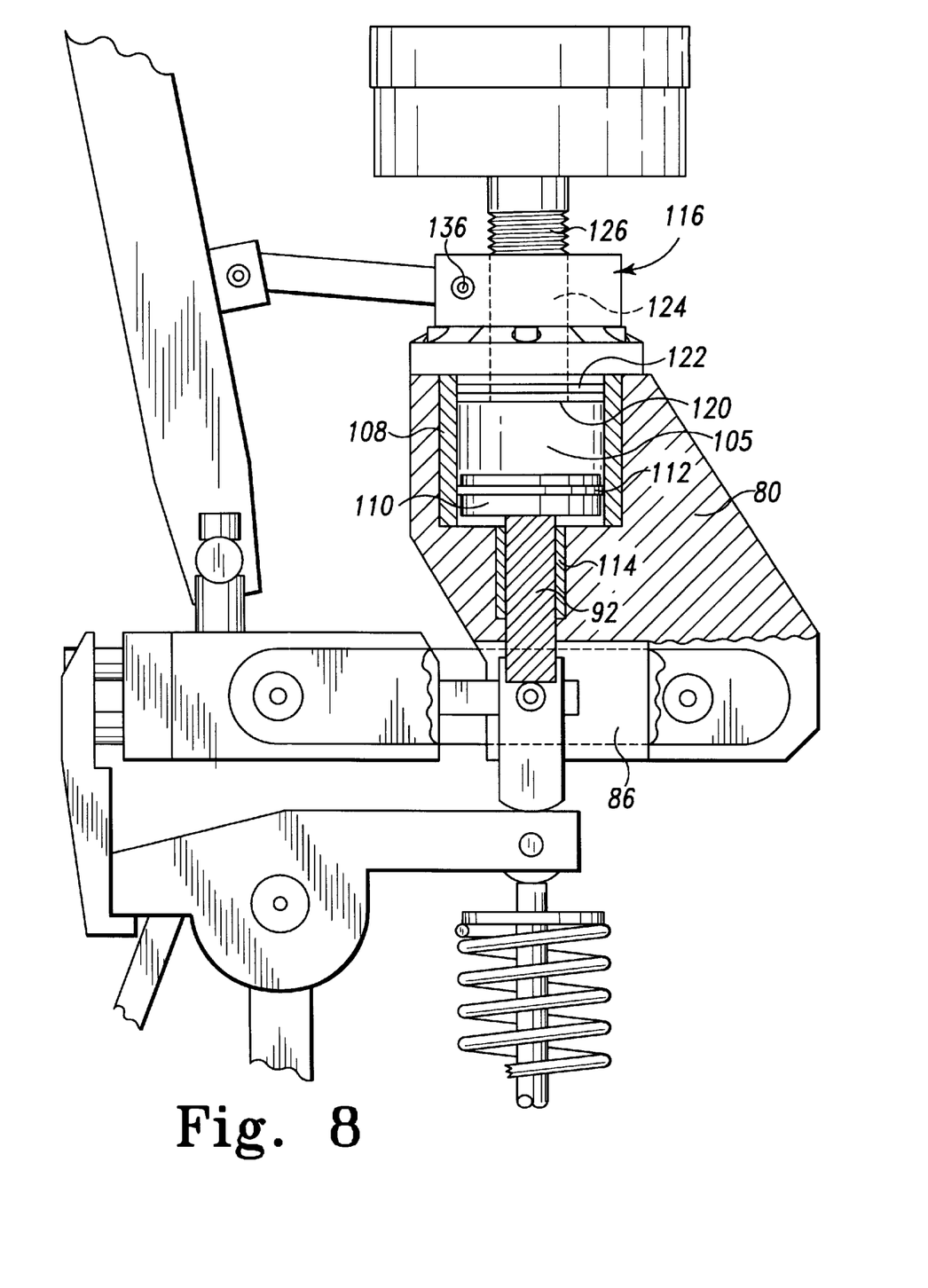
FIG. 8 is a diagrammatic side view, in partial cross section and with portions removed, of the valve spring tester of FIG. 1 operationally mounted on a valve shifting rocker arm assembly.

Referring now to FIG. 8, the interior configuration of main body 80 is further shown. Along its upper portion, main body 80 includes a cylindrical chamber 105 lined with stainless steel sleeve 108. Piston 110 vertically reciprocates within chamber 105. Teflon® O-ring 112 extends circumferentially around piston 110 and seals with sleeve 108 to prevent fluid leakage therebetween. A backing rubber O-ring (not shown) concentric with O-ring 112 is positioned between O-ring 112 and piston 110 to provide a fluid-tight seal therebetween. Piston shaft 92 projects from piston 110 and extends through bronze sleeve 114 installed within main body 80 and into cavity 86 as described above. To allow air to enter the portion of chamber 105 below piston 110 to prevent a vacuum from being formed thereat, an inlet bore (not shown) can be provided through the main body 80.

Capping main body 80 is an aluminum cylinder cap assembly, which is generally designated 116. Six cap screws 118 spaced at even intervals around cap assembly 116 engage tapped bores provided in the top surface of main body 80 to install cap assembly 116 on main body 80. An annular neck portion 120 of cap assembly 116 that is ringed by an elastomeric O-ring 122 projects into sleeve 108. O-ring 122 prevents fluid contained in chamber 105 above piston 110 from escaping between cap assembly 116 and main body 80. An internal hollow 124 of assembly 116 opens into chamber 105 at one end and is threaded at its opposite end to receive the threaded neck or socket 126 of gauge 128 (see FIG. 1). A pair of screw plugged bleeder ports 130, 132 (see FIG. 2) open into internal hollow 124. A single bleeder port alternatively may be employed within the scope of the present invention. When screws capping bleeder ports 130, 132 are removed, hydraulic fluid can be inserted through one of the uncapped bleeder ports into chamber 105 and hollow 124 and air may escape through the other uncapped bleeder port. After filling of tester 20 with hydraulic fluid, when ports 130, 132 are subsequently capped, tester 20 is essentially purged of any internal air bubbles which could influence the tester results. On its upper surface, cylinder cap assembly 116 is provided with facing flanges 134 that receive pivot pin 136 in an interference fit. Pivot pin 136 passes through the end of calibration link 40.

Figure 2:
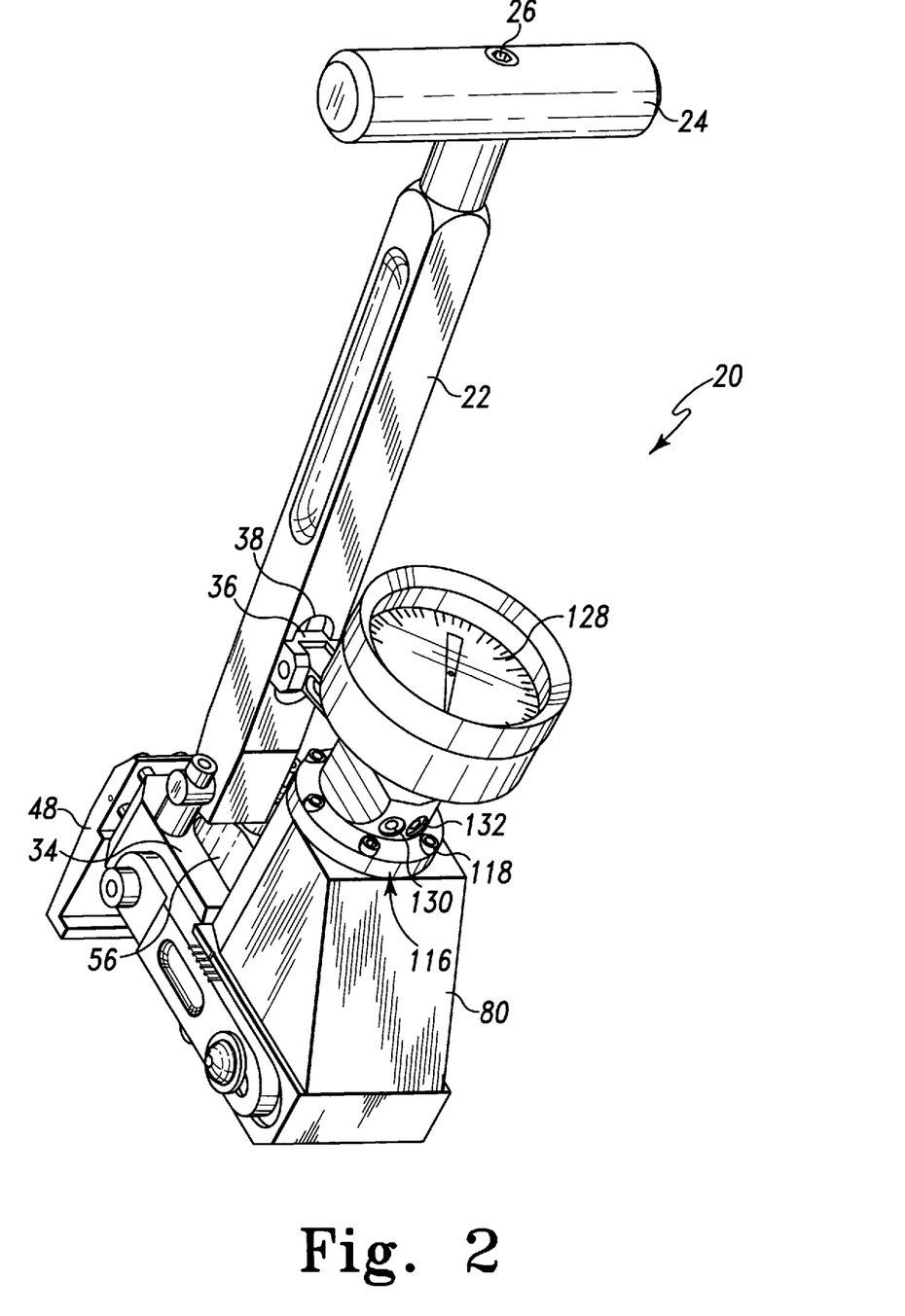
FIG. 2 is a top, front perspective view of the valve spring tester of FIG. 1.
Figure 3:
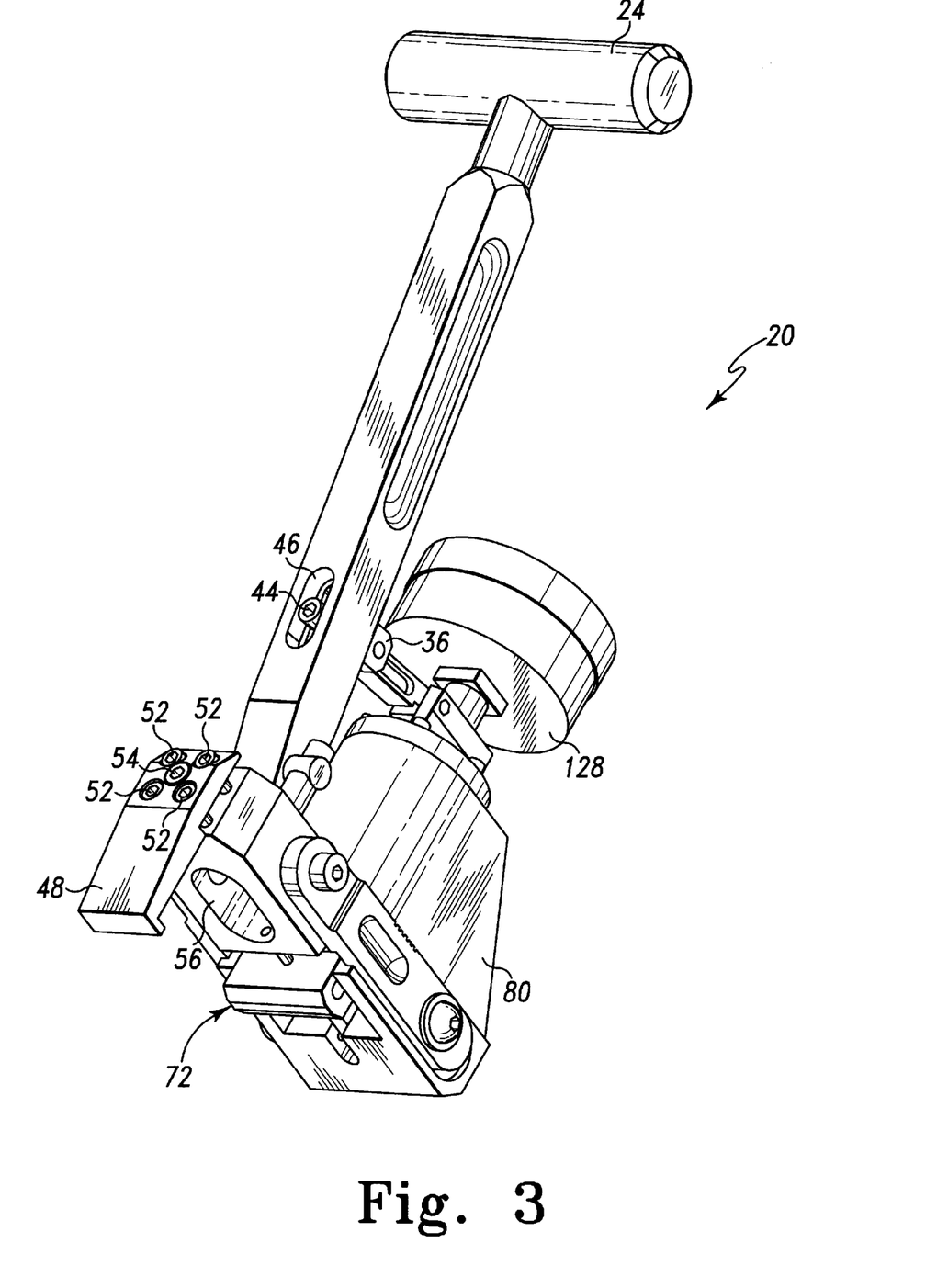
FIG. 3 is a bottom, rear perspective view of the valve spring tester of FIG. 1.
Figure 4:
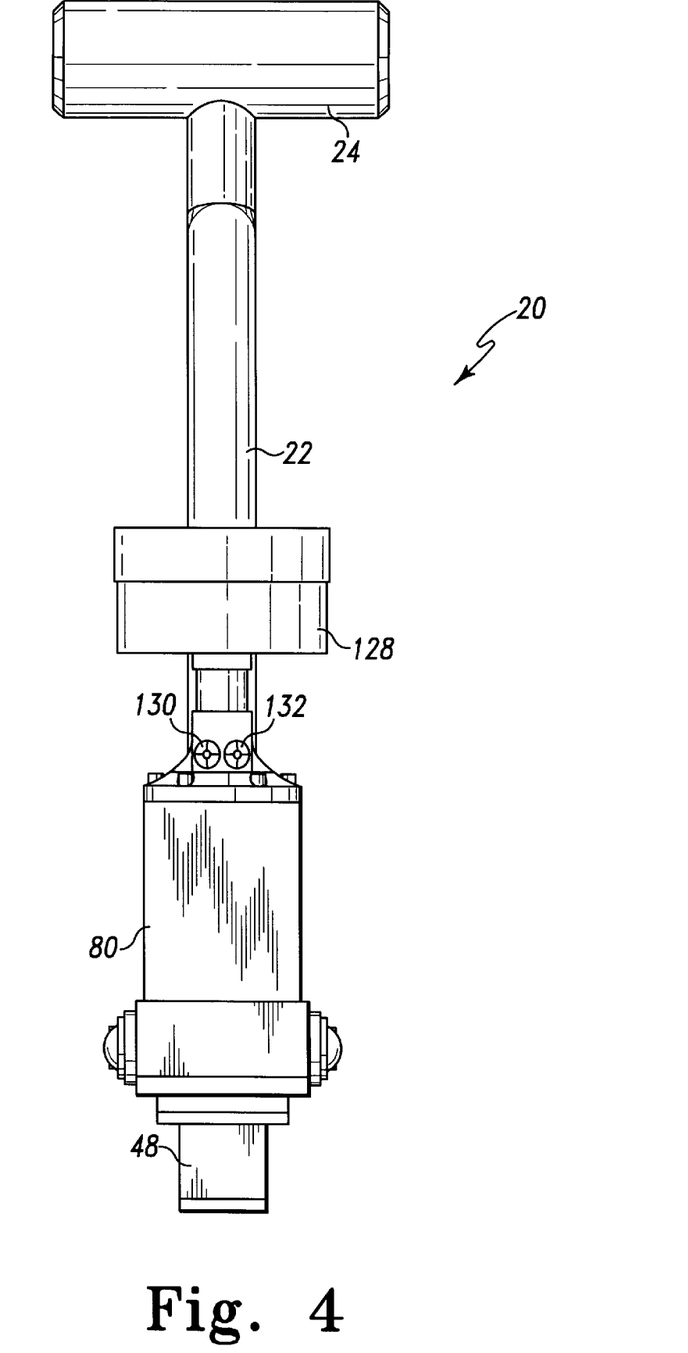
FIG. 4 is a front view of the valve spring tester of FIG. 1.
Figure 5:
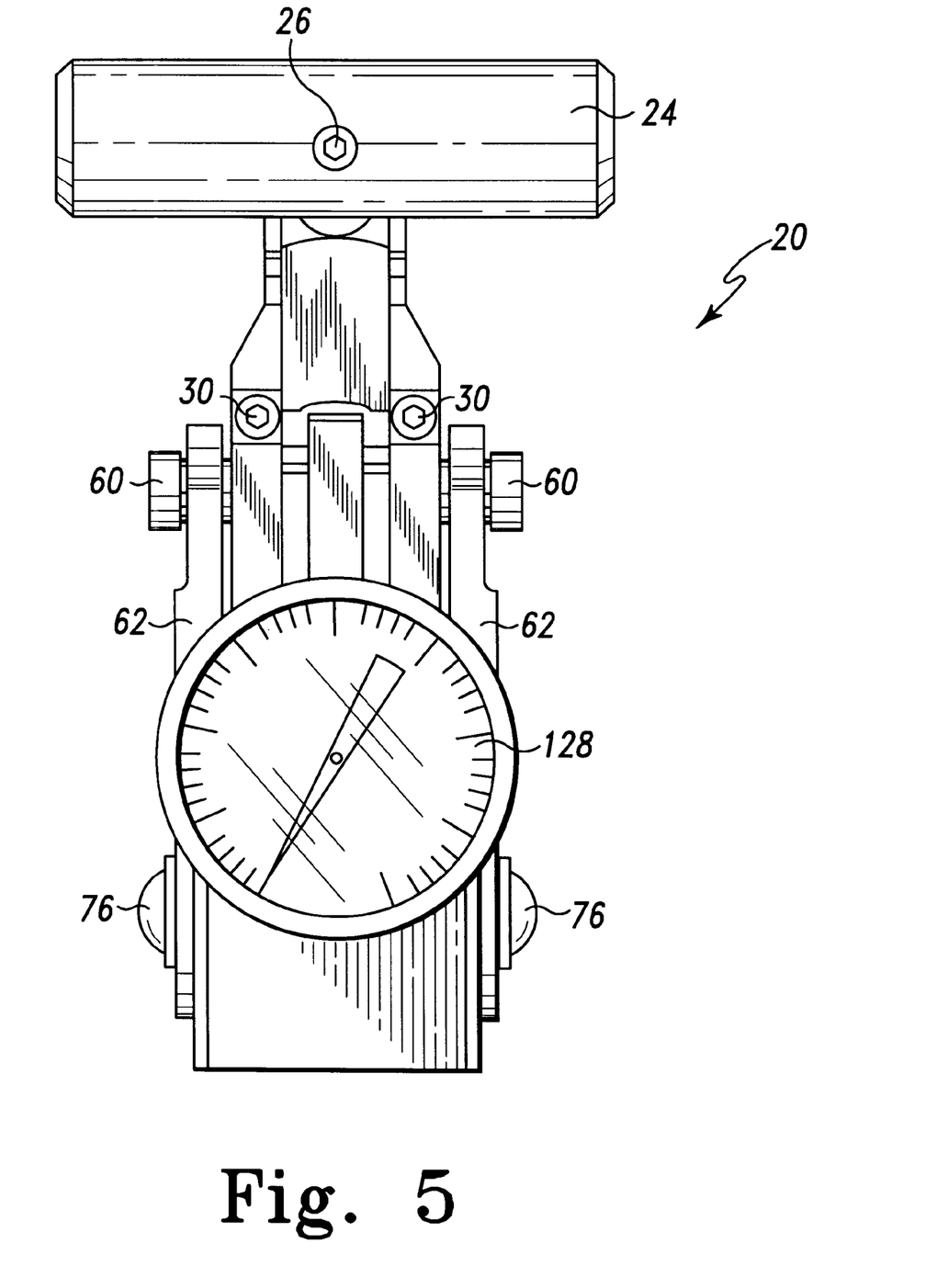
FIG. 5 is a top view of the valve spring tester of FIG. 1.

As shown in FIGS. 2 and 5, gauge 128 is an analog gauge and is a commercially available type of pressure gauge designed to display pounds per square inch pressure readings. Piston 110 is designed to have a hydraulic contacting surface area of one square inch, and therefore gauge 128 actually displays the pounds of force experienced by piston shaft 92 during operation as described further below. Other types of gauges or displays may be used within the scope of the present invention. For example, a strain gauge could be substituted for the shown cooperating piston and gauge within the scope of the present invention. Hydraulic fluids, such as oil, are preferably used to fill piston chamber 105 due to the general incompressibility of such fluids. However, in alternate embodiments, air or other gases could be utilized.

The structure of tester 20 will be further understood in view of the following description of its operation. FIG. 9 shows on head valve spring tester 20 after it has been operationally mounted on a rocker arm assembly generally designated 140. Assembly 140 includes a rocker arm stud 142 which is standardly secured to the cylinder head in a not shown fashion. Assembly 140 includes a first rocker arm 144 extending to the left from a trunnion portion 146 and a second rocker arm 148 extending to the right from trunnion portion 146. Rocker arm assembly 140 is mounted to the engine such that the rocker arms 144, 148 pivot together about trunnion 146. Proximate the distal end of rocker arm 148, roller tip 150 is revolvably mounted on transversely extending axle 152. Roller tip 150 directly contacts the upper end of valve stem 154, the lower end of which mounts to the valve. Retainer 156 secured to valve stem 154 is abutted by valve spring 158 that extends down to the engine block. A push rod that engages rocker arm 144 to cause the rocker arm assembly 140 to be pivoted clockwise from the perspective of a FIG. 9 viewer and thereby push down valve stem 154 to operate the valve during engine use is not shown.

Tester 20 is positioned by a user in the arrangement shown in FIG. 9 in the following manner. Typically, a mechanic or other person working on an engine will know the size of the rocker arm assembly, and more importantly know the dimension between the center of trunnion 146 and roller tip axle 152. Tester 20 will be adjusted to fit such a dimensioned rocker arm assembly by moving rocker contacting face 97 that distance from bolts 60. Specifically, cap screws 76 are loosened such that main body 80 may be shifted relative to trunnion body 34. This relative shifting is controlled such that groove 84 lines up with the appropriate groove 78 on connecting arm 62 to achieve a proper spacing of the main and trunnion bodies. Grooves 78 start at a horizontal distance (as measured in FIG. 1) from the axis of stripper bolts 60 equal to one and four hundred thousandths (1.400) inches and are located each tenth of an inch (0.1") thereafter up to two inches. (In the Figures, the last or right-most (in FIG. 1) groove 78 shown is only at 1.9 inches.) It will be appreciated that this distance corresponds to the horizontal distance between the axis of stripper bolts 60 (i.e., the point about which main body 80 pivots relative to trunnion body 34) and rocker contacting face 97. This sixth tenth inch range of rocker arm lengths is suitable to accommodate a large number of conventional rocker arm assemblies, but larger or smaller ranges may also be employed. It will be appreciated that for a rocker arm having a dimension of 1.4 inches between trunnion 146 and axle 152, tester 20 will be arranged such that groove 84 is aligned with the left most (in FIG. 1) groove 78.

After the desired spacing of main body 80 and trunnion body 34 is achieved, cap screws 76 are tightened. A user of tester 20 then maneuvers tester 20 such that rocker contacting surface 97 is aligned directly over roller axle 152 and in line with valve stem 154, and such that a rocker stud 142 (if present) is inserted through trunnion body opening 56. It will be appreciated that when so aligned, rocker stud 142 will be generally centered between stripper bolts 60. While the tester 20 is held in this operational position, adjustment screw 54 is rotated to cause rocker latch member 48 to be moved into the position shown in FIG. 9 where lip 50 projects below the underside of rocker arm 144. It will be appreciated that after main body 80 has been set relative to trunnion body 34, even if it is difficult to visually determine whether rocker contacting face 97 is disposed in alignment with axle 152 and valve stem 154, a user will be able to adequately align tester 20 on a generally horizontal rocker arm assembly by ensuring that stud 142 is generally between bolts 62 or trunnion 146 is positioned generally below opening 56. It will be appreciated that this horizontal adjustability of rocker latch member 48 allows rocker arm assemblies with different length rocker arms 144 to be accommodated by tester 20.

After tester 20 is arranged as shown in FIG. 9, a user grabs handle grip 24 and pulls (or pushes) in a direction generally to the right in FIG. 9. As force is applied, main body 80 and its connected components tend to rotate around trunnion body 34 due to the pivotal connection therewith. As this rotation occurs, rocker block assembly 72 does not move vertically due to its abutment against roller arm 148, but piston shaft 92 and piston 112 experience upward motion relative to the downwardly moving main body 80. The force on the handle is applied through rocker contacting face 97 onto rocker arm 148 and therefore against spring 158. As greater amounts of force are continued to be applied, the reading on gauge 128, which reflects the force applied on rocker arm 148 and therefore spring 158, continues to increase. At the point at which spring 158 finally gives or begins to compress, the gauge reading is mentally noted as to identify the spring force. An experienced user will quickly learn to feel when the spring initially gives such that determination of the force is possible.

To calibrate tester 20 prior to its distribution, calibration link 40 is utilized in testing procedures. A spring with a known spring constant is tested. After being arranged as shown in FIG. 9 over the test spring, handle 22/24 is pulled and readings are taken as described above. By loosening screw 44, moving pivot mount 36, and then tightening screw 44, calibration link 40 is manipulated to effectively change the point about which handle arm 22 pivots to thereby cause a change in the lever arm lengths through which forces are applied on the tester components.

An understanding of the reason for this calibration technique will be advanced in view of the following general description. If handle arm 22 were vertically mounted directly to main body 80, as handle grip 24 is pulled to the right in FIG. 1, a component of the force resulting on latch member 48 is pivoted through stripper bolt 60 to generate a downward force on rocker block assembly 72, which causes valve spring 158 to compress without transferring force to piston shaft 92. As a result, this force on the spring is not registered on gauge 128. A force which similarly fails to register also apparently results when handle 22/24 is mounted as shown on tester 20.

Figure 1:
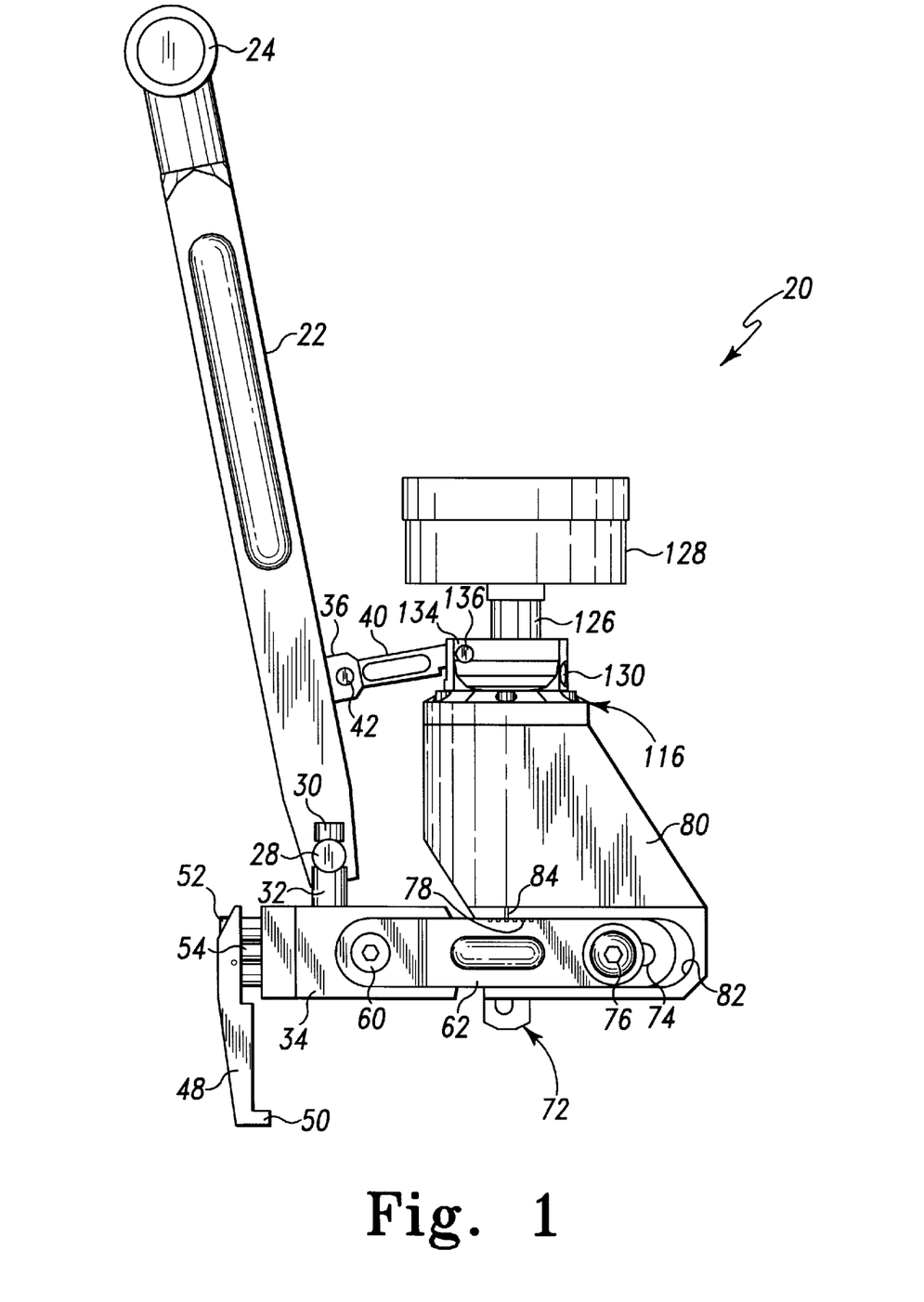
FIG. 1 is a side view of a first embodiment of an on head valve spring tester of the present invention.

The shown tester 20 is particularly adapted to counter this non-registering force. There are three interrelated distances which generally affect this force countering feature of tester 20, namely the distance from handle grip 24 to pivot pin 42, the distance from pivot pin 42 to pivot shaft 28, and the distance from pivot shaft 28 to stripper bolt 60. Handle arm 22 works as a lever in which pivot pin 42 is the fulcrum. With reference to FIG. 1, as force is applied to the right on handle grip 24, a force acting to the left on pivot shaft 28 results. This force is pivoted through stripper bolts 60 and causes an upward force on rocker block assembly 72 that is transferred to piston shaft 92. This force on piston shaft 92 creates a display on gauge 128 of a force which is not actually being applied to compress valve spring 158. The lesser the distance is from pivot pin 42 to pivot shaft 28, or the greater the distance from pivot shaft 28 to stripper bolts 60, the higher the force registered on gauge 128. Tests with different handle pivot points are conducted until the positioning is found when the gauge reading equals the known spring constant for that spring. At such a point, it will be recognized that for lateral forces on the handle grip, the force acting to compress spring 158 without being applied to piston shaft 92 as described above is substantially equal to that force applied to piston shaft 92 that does not act on the spring as described above. At that point, no further adjustments are required. Tester 20 may be used with different sized rocker arms simply by adjusting rocker latch member 48 and main body 80 relative to trunnion body 34 as described above.

Referring now to FIG. 10, there is shown a bottom view of a second embodiment of a valve spring tester, generally designated 200, of the present invention. Tester 200 will be understood to be substantially the same as tester 20. For this reason, the description will be focused on the differences, and a primed notation is adopted for identification of those parts to tester 200 which correspond to what has already been described in connection with tester 20. Tester 200 includes an opening 56' which opens all the way to the forward end of trunnion body 34'. This configuration, as opposed to the smaller opening of tester 20, facilitates the insertion of rocker arm studs. Main body 80' is provided with a rearwardly extending bore 210 in which inserts a spacer rod 211 that at its rearward end abuts the forward face of rocker block assembly 72'. The forward end of rod 211 is exposed to permit its rotation to adjust the position of rod 211 relative to the main body 80'. To accomplish this adjustability, at least a portion of the axial lengths of rod 211 and bore 210 are cooperatively threaded. During the initial set-up of tester 200, rod 211 is axially adjusted such that rocker block assembly 72' is properly positioned relative to the piston shaft (not shown), and once so positioned no further rod adjustments are required. An additional difference between tester 200 and tester 20 is the inclusion of a wear cylinder 214 made of steel. Wear cylinder 214 is friction fit within a concave recess provided at the bottom end of the aluminum rocker block assembly 72', and is that portion of the assembly 72' which directly engages the upper surface of the rocker arm during valve spring testing. Latch member 48' if provided with an arcuate notch 220 within lip 50' to better accommodate push rods used to actuate the rocker arm assembly. An adjustment screw knob 222 used to adjust the spacing between latch member 48' and trunnion body 34' is also shown.

While this invention has been shown and described as having preferred designs, the present invention may be modified within the spirit and scope of this disclosure. For example, other handle configurations naturally may be employed provided their possible impact on force distributions and the gauge readings is taken into account. The shown configuration, which utilizes a generally upright handle, is preferred because typically it is not interfered with by any portion of the engine in which the valve springs are mounted. However, with adaptions, handle orientations such as extending directly from the main body to the right in FIG. 9 may be employed within the scope of the invention. Moreover, the handle need not be pivotally connected to the tester body, but may be fixedly connected in alternate embodiments. This application is therefore intended to cover any variations, uses, or adaptations of the invention using its general principles. Further, this application is intended to cover such departures from the present disclosure as come within known or customary practice in the art to which this invention pertains.

What is claimed is:

1. An apparatus for on head testing of a valve spring that biases a rocker arm assembly, comprising:

a body;

a biasing member connected to said body and engageable with a first rocker arm of the rocker arm assembly;

a latch member connected to said body and engageable with a second rocker arm of the rocker arm assembly;

wherein at least one of said latch member and said biasing member is structured and arranged to be movable relative to said body to alter a spacing between said latch member and said biasing member for accommodating different length rocker arms;

a handle connected to at least one of said latch member and said body for driving said biasing member toward the first rocker arm during valve spring testing;

an indicator for measuring and displaying a force applied on the rocker arm assembly to compress the valve spring during valve spring testing; and at least one guide pin and a threaded adjustment member having an axial length, said at least one guide pin fixed to said latch member and extending into a bore within said body, said threaded adjustment member axially fixed to said latch member and axially extending into a threaded bore within said body, wherein rotation of said adjustment member moves said latch member relative to said body.

2. An apparatus for on head testing of a valve spring that biases a rocker arm assembly, comprising:

a body;

a biasing member connected to said body and engageable with a first rocker arm of the rocker arm assembly;

a latch member connected to said body and engageable with a second rocker arm of the rocker arm assembly;

wherein at least one of said latch member and said biasing member is structured and arranged to be movable relative to said body to alter a spacing between said latch member and said biasing member for accommodating different length rocker arms;

a handle connected to at least one of said latch member and said body for driving said biasing member toward the first rocker arm during valve spring testing;

an indicator for measuring and displaying a force applied on the rocker arm assembly to compress the valve spring during valve spring testing;

wherein said body comprises a trunnion body portion and a main body portion, wherein said latch member extends from said trunnion body portion, and wherein said biasing member projects from said main body portion;

at least one connecting element extending between said trunnion body portion and said main body portion, wherein said connecting element is pivotally mounted to said trunnion body portion to permit a rotational motion of said main body portion relative to said trunnion body portion; and wherein said connecting element comprises a slot, wherein at least one fastener for securing said connecting element to said main body portion extends through said slot and into engagement with said main body portion, and wherein a positioning of said main body portion relative to said trunnion body portion is adjustable by changing a positioning of said at least one fastener along a length of said slot.

3. The apparatus of claim 2 wherein said main body portion and said at least one connecting element comprise cooperating indicia to visibly indicate spacing between said main body portion a nd said trunnion body portion.

4. An apparatus for on head testing of a valve spring that biases a rocker arm assembly, comprising:

a body;

a biasing member connected to said body and engageable with a first rocker arm of the rocker arm assembly;

a latch member connected to said body and engageable with a second rocker arm of the rocker arm assembly;

wherein at least one of said latch member and said biasing member is structured and arranged to be movable relative to said body to alter a spacing between said latch member and said biasing member for accommodating different length rocker arms;

a handle connected to at least one of said latch member and said body for driving said biasing member toward the first rocker arm during valve spring testing;

an indicator for measuring and displaying a force applied on the rocker arm assembly to compress the valve spring during valve spring testing;

wherein said body comprises a trunnion body portion and a main body portion, wherein said latch member extends from said trunnion body portion, and wherein said biasing member projects from said main body portion; and wherein said handle comprises a handle arm pivotally mounted to said trunnion body portion, and further comprising a calibration link having first and second ends, said link first end being pivotally mounted to said handle arm and said link second end being pivotally mounted to said main body portion.

5. The apparatus of claim 4 further comprising means for adjusting along a length of said handle arm a positioning of said pivotally mounting of said ink first end.

6. An on head valve spring tester for use with a rocker arm assembly comprising first and second rocker arms comprising:

a body;

a biasing member movably mounted to said body and adapted for abutting engagement with the first rocker arm;

a latch member extending from said body for engagement with the second rocker arm;

a handle connected to at least one of said latch member and said body for driving said biasing member in a first direction toward the first rocker arm during valve spring testing;

wherein said biasing member is movable relative to said body in a direction generally opposite to said first direction from a first position toward a second position during biasing engagement with the first rocker arm during valve spring testing;

an indicator adapted to detect movement of said biasing member from said first position toward said second position and provide a display indicative of a force required to so move said biasing member; and wherein said indicator comprises a piston, a piston shaft extending from said piston, and a gauge, wherein said piston shaft is structured and arranged to engage said biasing member, wherein said piston is housed within a chamber internal to said body, wherein said chamber ports to said gauge, and wherein movement of said biasing member moves said piston shaft and said piston to change the effective volume of said chamber between said piston and said gauge.

7. The on head valve spring tester of claim 6 wherein said piston comprises a chamber facing surface area of one square inch, and wherein said gauge comprises a pressure gauge adapted to display pressure in pounds per square inch, whereby a pressure reading on said gauge translates directly to a force in pounds applied to said piston shaft.

8. An on head valve spring tester for use with a rocker arm assembly comprising first and second rocker arms, comprising:

a body;

a biasing member movably mounted to said body and adapted for abutting engagement with the first rocker arm;

a latch member extending from said body for engagement with the second rocker arm;

a handle connected to at least one of said latch member and said body for driving said biasing member in a first direction toward the first rocker arm during valve spring testing;

wherein said biasing member is movable relative to said body in a direction generally opposite to said first direction from a first position toward a second position during biasing engagement with the first rocker arm during valve spring testing;

an indicator adapted to detect movement of said biasing member from said first position toward said second position and provide a display indicative of a force required to so move said biasing member; and wherein said biasing member comprises opposite side edges defining pin receiving channels, and further comprising pins inwardly projecting into said channels from sections of said body flanking said biasing member.

9. An on head valve spring tester for use with a rocker arm assembly comprising first and second rocker arms, comprising:

a body;

a biasing member movably mounted to said body and adapted for abutting engagement with the first rocker arm;

a latch member extending from said body for engagement with the second rocker arm;

a handle connected to at least one of said latch member and said body for driving said biasing member in a first direction toward the first rocker arm during valve spring testing;

wherein said biasing member is movable relative to said body in a direction generally opposite to said first direction from a first position toward a second position during biasing engagement with the first rocker arm during valve spring testing;

an indicator adapted to detect movement of said biasing member from said first position toward said second position and provide a display indicative of a force required to so move said biasing member; and wherein said body comprises a trunnion body portion and a main body portion, wherein said latch member extends from said trunnion body portion, wherein said biasing member projects from said main body portion, and further comprising at least one guide rod projecting forward from said trunnion body portion, wherein said biasing member comprises an opening shaped complementary to said at least one guide rod, said at least one guide rod and said biasing member opening structured and arranged to permit said biasing member to move axially along said at least one guide rod and to prevent said biasing member from moving radially from said at least one guide rod.

10. An on head valve spring tester for use with a rocker arm assembly comprising first and second rocker arms, comprising:

a body;

a biasing member movably mounted to said body and adapted for abutting engagement with the first rocker arm;

a latch member extending from said body for engagement with the second rocker arm;

a handle connected to at least one of said latch member and said body for driving said biasing member in a first direction toward the first rocker arm during valve spring testing;

wherein said biasing member is movable relative to said body in a direction generally opposite to said first direction from a first position toward a second position during biasing engagement with the first rocker arm during valve spring testing;

an indicator adapted to detect movement of said biasing member from said first position toward said second position and provide a display indicative of a force required to so move said biasing member; and wherein said body comprises a trunnion body portion and a main body portion, wherein said latch member extends from said trunnion body portion, wherein said biasing member projects from said main body portion, and further comprising at least one connecting element extending between said trunnion body portion and said main body portion, wherein said connecting element is pivotally mounted to said trunnion body portion to permit a rotational motion of said main body portion relative to said trunnion body portion, and wherein said handle comprises a handle arm pivotally mounted to said trunnion body portion, and further comprising a calibration link having first and second ends, said link first end being pivotally mounted to said handle arm and said link second end being pivotally mounted to said main body portion.

11. An on head valve spring tester comprising:

a handle;

means for attaching to a first rocker arm;

means, operable by said handle, for biasing a second rocker arm fixedly connected with the first rocker arm;

means for displaying a force applied by said biasing means on the second rocker arm;

means for pivotally connecting said biasing means to said attaching means;

a calibration link pivotally mounted at opposite ends to said handle and said biasing means; and wherein said handle is pivotally mounted to said attaching means.

12. An on head valve spring tester comprising:

a handle;

means for attaching to a first rocker arm;

means, operable by said handle, for biasing a second rocker arm fixedly connected with the first rocker arm;

means for displaying a force applied by said biasing means on the second rocker arm, said displaying means comprising a gauge connected to a chamber, and a piston operatively connected to said biasing member and moveable within said chamber.

\* \* \* \* \*